United States Patent [19]

Andersson et al.

[11] 4,138,287

[45] Feb. 6, 1979

[54] PURIFYING AND ISOLATING METHOD FOR HEPATITIS VIRUS TO USE IN PREPARING VACCINE

[75] Inventors: Lars-Olov Andersson, Knivsta; Gudrun M. Einarsson; Lennart P. Kaplan, both of Upsala, all of Sweden

[73] Assignee: AB Kabi, Stockholm, Sweden

[21] Appl. No.: 777,670

[22] Filed: Mar. 15, 1977

[30] Foreign Application Priority Data

Mar. 18, 1976 [DE] Sweden .............................. 7603386

[51] Int. Cl.² ..................... C12K 7/00; A61K 39/12
[52] U.S. Cl. ...................................... 195/1.5; 424/89
[58] Field of Search ............................ 195/1.5; 424/89

[56] References Cited

U.S. PATENT DOCUMENTS

| | | | |
|---|---|---|---|
| 3,636,191 | 1/1972 | Blumberg et al. | 424/89 |
| 3,925,152 | 12/1975 | Porath et al. | 195/1.5 |
| 3,976,767 | 8/1976 | Neurath | 195/1.5 |

*Primary Examiner*—Sam Rosen
*Attorney, Agent, or Firm*—A. A. Orlinger

[57] ABSTRACT

Hepatitis B virus (detectable as its surface antigen $HB_sAg$) is produced in a purification preferably suitable for use in preparing a hepatitis vaccine, by contacting a crude biological starting material containing hepatitis B virus with a water-insoluble cross-linked sulfated polysaccharide gel matrix adsorbing agent to adsorb the hepatitis B virus thereon and then desorbing that virus therefrom by treating that hepatitis B virus carrying adsorbent with a desorbing agent.

10 Claims, No Drawings

PURIFYING AND ISOLATING METHOD FOR HEPATITIS VIRUS TO USE IN PREPARING VACCINE

This invention is that of a method of purifying and isolating hepatitis B virus, detectable as its surface antigen, $HB_sAg$, from a crude starting biological material containing that virus to provide it in a purified state suitable for use preferably in preparing hepatitis vaccine.

More specifically the invention is a method of isolating hepatitis B virus from such crude starting biological material by contacting a water-insoluble cross-linked sulfated polysaccharide gel matrix adsorbing agent to adsorb the hepatitus B virus thereon and then desorbing that virus from that desorbing agent by treating that hepatitis B virus carrying adsorbent with a desorbing agent.

Hepatitis virus type B, also called serum hepatitis, is spread through such biological materials as blood, plasma, serum, urine and feces. Type B virus also can be spread through plasma fractions used in medical treatment. It can be found in waste products containing biological material and in concentrations sufficient to spread the infention.

Hepatitis B virus consists of an inner core containing nucleic acid and protein and an outer protein coat. Lipidic material also can be found in this virus but distribution of the lipid is not fully investigated.

In persons with acute hepititis, intact hepatitis virus is produced, but the main part of the produced virus material consists of protein from the outer coat. Excess production of this coat protein makes it possible to detect hepatitis B virus-infected material by different immunonoligical methods. The method first used was radial immunodiffusion, ID (Berg et al., Vox. Sang. Vol. 22 (1972) p. 1), which method has been followed by considerably more sensitive radio-immunological techniques.

Hepatitis B is a serious disease. Mortality is comparatively low but the time of convalescence is long, and lasting damage to the liver is not unusual. Medicines specific for hepatitis do not yet exist. There are, however, certain possibilities of prophylactic treatment. Promising results have been obtained by prophylactic use of immunoglobulin to hepatitis B. However, the protection is of rather short duration. Furthermore, this method of treatment hardly can be used for the prevention of hepatitis B in larger professional or population groups. One solution to this problem could be a vaccine.

Theoretically, vaccine against hepatitis B can be produced by first isolating the hepatitis B virus material and to inactivate it in a suitable way, or by separating the intact virus from excess of its coat protein. Vaccination with such material can induce production of antibodies against hepatitis B virus, thereby to provide protection from hepatitis B infection. One problem is isolating the virus material in a pure state without disturbing its structure.

All of the known methods for purifying hepatitis B virus material are rather complicated and also difficult to operate on a commercial scale. The most widespread technique is based on separation by ultracentrifugation in a density gradient. However, this requires expensive equipment. For raw material, blood from persons with demonstrable hepatitis B virus surface antigen, $HB_sAg$, has been used.

Earlier, methods have been developed irreversibly to bind and remove $HB_sAg$-positive material from biological material containing it. The purpose of this was to bind the hepatitis virus to added material without risking leakage, in order to render the virus harmless by combustion or chemical inactivation.

In connection with our studying the possibility of binding of hepatitis B virus material to different adsorbents we found that hepatitis B virus surface antigen, $HB_sAg$, was adsorbed to water-insoluble gels comprised of a sulfated polysaccharide argarose conjugate. The adsorbed virus material then easily could be eluted from the gel by desorption with a buffer containing sodium chloride. The resulting purity of the thus isolated hepatitis B virus was very high in that purification of at least 30 times was obtained. This is of great importance because then further purification is achieved by working with concentrated solutions.

Thus, the method is well suited for operation on a larger scale. Then still further purification by using available steps results in a practically pure preparation of hepatitis B virus surface antigen, suitable for use to produce a vaccine. Thus, the process of this invention has the advantage over methods hitherto used in that it is both easy to work on a large scale (e.g. commercially), requires no expensive special equipment, and is low in cost.

Considered broadly, the method of the invention comprises providing hepatitis B virus in a purification for it to be suitable for use in preparing a hepatitis vaccine, by contacting a starting crude biological material containing that virus with a water-insoluble cross-linked sulfated polysaccharide gell matrix adsorbing agent for said virus and in an amount sufficient to adsorb beneficially more than the major part and to about substantially the entire content of said virus from said starting material and for a time sufficient for said extent of that virus to be adsorbed therefrom onto said adsorbing agent; and separating said virus from said agent.

The following examples illustrate, without limiting, the invention:

EXAMPLE 1—Adsorption of $HB_sAg$ from plasma by column packed cross-linked agarose-dextran sulfate conjugate, followed by direct desorption:

Preparation of gel-dextran sulfate conjugate: The cross-linked dextran sulfate adsorbent conjugate was produced by first mixing 2 g. of dextran sulfate dissolved in 150 ml. of 0.5 M sodium carbonate with 100 ml. of SEPHAROSE 4B CL beads (identified shortly below, product of Pharmacia Fine Chemicals, Piscataway, N.J. and Uppsala, Sweden) equilibrated with 0.5 M sodium carbonate. Then, 5 g. of cyanogen bromide dissolved in 50 ml. of distilled water was added. The pH of the mixture was adjusted to 11 with 5 M sodium hydroxide solution and maintained constant at this value for 15 minutes. Thereafter the pH was allowed to decline. The gel suspension was then left at room temperature and stirred for 17 hours, and thereafter thoroughly washed.

SEPHAROSE 4B CL beads are agarose gel beads provided by allowing a 4% aqueous solution of agarose to gel in the form of beads of from 40 to 190 microns in particle size in wet state (i.e. as swollen by water), and which are cross-linked by reaction with epibromhydrin.

Purification and Isolation of $HB_sAg$: An $HB_sAg$-positive blood plasma (from a chronic carrier of hepatitis virus) was used as starting material. The titer compared with a standard antigen was 1:16 determined by the double immunodiffusion technique (ID).

A chromatographic column (diameter 26 mm) was filled with 100 ml. of the beads of cross-linked agarose-dextran sulfate conjugate adsorbent, equilibrated in a buffer consisting of an aqueous solution of 0.05 M Tris, 0.02 M sodium citrate and 0.10 M sodium chloride, pH of 7.5. (Hereinafter this Tris buffer is merely referred to as buffer). Using a flow-rate of 50 ml/hour, 200 ml. of blood plasma containing hepatitis B virus was applied to the column. Then 500 ml. buffer was passed through at reduced flow rate of 25 ml/hour, and the adsorbed material then was eluted with a buffer containing only 0.5 M sodium chloride.

Consecutive fractions of 5 ml. each of the eluate were taken and submitted to $HB_sAg$-testing (by ID and by CEP) and collected so long as the test was positive. These $HB_sAg$-positive fractions of the eluate were pooled and the hepatitis virus material therein was precipitated by admixing ammonium sulfate (22 g/100 ml. of pooled positive eluate fractions). The precipitate was collected by centrifugation and (after decanting the supernatant) was dissolved in 20 ml. of buffer. The resulting solution was gel filtered on a column (diameter 50 mm) filled with SEPHAROSE 6B CL (product of Pharmacia, supra) to a height of 850 mm and first equilibrated with buffer.

SEPHAROSE 6B CL beads are the same as SEPHAROSE 4B CL beads except for being prepared from a 6% aqueous solution of agarose (thus being denser beads with consequently finer pores) and having particle size of from 40 to 210 microns in the wet state.

Consecutive fractions of 5 or 10 ml. each of the effluent (from the gel filtration) were taken and submitted to $HB_sAg$-testing (as above) and collcted so long as the test was positive. The resulting $HB_sAg$-positive fractions were examined by electron microscopy and found to contain practically pure hepatitis virus material, suitable for use in preparing hepatitis vaccine.

Example 2—Batchwise adsorption of $HB_sAg$ from plasma by cross-linked agarose-dextran sulfate conjugate, followed by direct elution:

Preparation of gel-dextran sulfate conjugate adsorbent: Agarose-dextran sulfate conjugate adsorbent was prepared as in Example 1.

Purification and isolation of $HB_sAg$: To 200 ml. $HB_sAg$-positive blood plasma with a titer of 1:16 (determined by ID) was added 100 ml. of the agarose-dextran sulfate adsorbent equilibrated with buffer as in Example 1. After stirring for 30 minutes, the equilibrated hepatitis virus bearing gel derivative conjugate adsorbent was transferred to a glass filter funnel and washed with 5 × 200 ml. buffer. Thereafter desorption was carried out, using 2 × 100 ml. buffer now with 1 M sodium chloride content (along with its Tris and sodium citrate). Into the eluate 42 g. ammonium sulfate was admixed. The resulting precipitate was collected, dissolved in 20 ml. of buffer and gel filtered as in Example 1 including also the taking and testing of collected fractions of effluent.

These $HB_sAg$-positive fractions were studied by electron microscopy and found to contain practically pure hepatitis virus material, suitable for use in preparing hepatitis vaccine.

EXAMPLE 3—Adsorption of $HB_sAg$ from plasma by agarose-heparin-conjugate, packed in a column, followed by salt-gradient elution:

Preparation of gel derivative adsorbent: The agarose-heparin conjugate adsorbent was prepared by mixing 100 ml. solution of heparin in water (5,000 units/ml.) with 100 ml. of SEPHAROSE 4B beads (swollen) and 4 g. of cyanogen bromide. The pH was adjusted to 11 and maintained constant at this value for 10 minutes, and then allowed to decline. Thereafter, the gel suspension was left at room temperature, stirred for 20 hours and then thoroughly washed.

Purification and isolation of $HB_3Ag$: An $HB_sAg$-positive blood plasma with a titer of 1:128 (by ID) was used as starting material. A chromatographic column (diameter 26 mm) was filled with 100 ml. of the gel derivative adsorbent, equilibrated with buffer as in Example 1. 20 ml. of the blood plasma was applied to the column at a flow rate of 50 ml/hour. Thereafter, 200 ml. of buffer was allowed to pass through before the adsorbed material was eluted with a linear gradient of buffer containing its sodium chloride in a final concentration of 2 M. The $HB_sAg$-positive fractions (taken as in Example 1) were examined by electron microscopy and the gel filtration effluent $HB_sAg$-positive material was found to consist of practically pure hepatitis virus material, suitable for use in preparing hepatitis vaccine.

EXAMPLE 4—Adsorption of $HB_sAg$ from plasma by agarose-chondroitin sulfate-conjugate, packed in a column, followed by direct desorption:

Preparation of gel conjugate adsorbent: The agarose-chondroitin sulfate conjugate adsorbent was prepared by first mixing 0.8 g. of chondroitin sulfate, dissolved in 15 ml. of 0.5 M sodium carbonate, with 30 ml. SEPHAROSE 4B CL beads (swollen) equilibrated with 0.5 M sodium carbonate. Thereafter, 1.6 g. of cyanogen bromide dissolved in 15 ml. of distilled water was added. The pH of the gel suspension was adjusted to 11 with 2.5 M sodium hydroxide solution and maintained constant at this value for 10 minutes. Then it was allowed to decline. The mixture was left at room temperature and stirred for 16 hours and then thoroughly washed.

Purification and isolation of $HB_sAg$: An $HB_sAg$-positive blood plasma (from a chronic carrier of hepatitis virus) was used as starting material. The titer compared with a standard antigen was 1:32 determined by ID.

A chromatrographic column (diameter 16 mm) was filled with 30 ml. of the agarose-chondroitin sulfate conjugate adsorbent equilibrated in buffer as in Example 1. 3 ml. of that blood plasma was applied at a flow rate of 12 ml/hour. Thereafter, 60 ml. of buffer was allowed to pass through before the adsorbed material was eluted with buffer with its sodium chloride now being 1 M. The $HB_sAg$-positive fractions of the eluate were pooled, and lipoproteins were precipitated therefrom by admixing 8% polyvinyl pyrrolidone, separated and discarded.

The filtrate solution was examined by electron microscopy and found to contain practically pure hepatitis virus material, suitable for use in preparing hepatitis vaccine.

The blood plasma used in any of the examples can be replaced by a correspondingly suitable amount of any of the other available starting crude biological material containing hepatitis B virus such as blood, blood plasma fractions, blood serum, or urine and processed correspondingly similarly to provide from these related sources in relatively similar manner a practically pure hepatitis B virus suitable for use in preparing a hepatitis vaccine.

In the preparation of the sulfated polysaccharide agarose conjugate adsorbent by mixing the polysaccharide with the cyanogen bromide, adjusting the pH and then allowing it to decline, the examples describe stirring the gel at room temperature for 20 hours. That stirring can be intermittent or omitted for it is not absolutely needed but usually done.

While the examples show taking 5 ml. fractions of eluate, their size can be varied at any convenient size and even as much as up to 10 ml. or so.

The agent used for desorbing the hepatitis B virus from the sulfated polysaccharide water-insoluble porous gel conjugate adsorbent generally is aqueous and non-reactive with the hepatitis virus and also the conjugate adsorbing agent.

While the invention has been explained by detailed description of certain specific embodiments of it, it is understood that various modifications and/or substitutions may be made within the scope of the appended claims which are intended also to embrace equivalents of the described embodiments.

What is claimed is:

1. A method of isolating hepatitis B virus (detectable as its surface antigen $HB_sAg$) from a starting crude biological material containing that virus, which method comprises (a) contacting the starting hepatitis virus containing material with a water-insoluble cross-linked sulfated polysaccharide agarose conjugate, porous gel adsorbing agent for said virus, to adsorb hepatitis virus from the starting material, and (b) desorbing the hepatitis B virus from said adsorbing agent by an aqueous solution desorbing agent for said virus, non-reactive with the virus and the sulfated polysaccharide gel adsorbing agent.

2. The method as claimed in claim 1, wherein the starting crude biological material containing the hepatitis B virus is selected from blood, blood plasma, blood plasma fractions, blood serum, urine and feces.

3. The method as claimed in claim 2, wherein the starting biological material is blood plasma.

4. The method as claimed in claim 3, wherein the hepatitis B virus is desorbed from the water-insoluble cross-linked sulfated polysaccharide porous gel adsorbing agent by eluting said adsorbent agent bearing the adsorbed virus with an aqueous buffer containing from 0.5 M to 2 M sodium chloride.

5. The method as claimed in claim 4, wherein the said sulfated polysaccharide gel adsorbing agent is supported in a chromatographic column before being contacted by the starting blood plasma, then equilibrated with an aqueous buffer solution for pH 7.5 and containing 0.05 M Tris, 0.02 sodium citrate and 0.01 M sodium chloride, and the starting blood plasma containing the hepatitis virus is applied to the thus equilibrated adsorbing agent and thereafter eluted therefrom with a buffer containing only 0.5 M sodium chloride.

6. The method of isolating hepatitis B virus (detectable as its surface antigen $HB_sAg$) from a starting crude biological material containing that virus, which method comprises (a) contacting the starting hepatitis virus containing material with a water-insoluble cross-linked sulfated polysaccharide agarose conjugate porous gel adsorbing agent for said virus and selected from agarose dextran sulfate, agarose chondroitin sulfate, or agarose heparin, to adsorb hepatitis virus from the starting material, and (b) desorbing the hepatitis B virus from said adsorbing agent by an aqueous solution desorbing agent for said virus, non-reactive with the virus and the sulfated polysaccharide gel adsorbing agent.

7. The method as claimed in claim 6, wherein the sulfated polysacharide is cross-linked by cyanogen bromide.

8. The method as claimed in claim 6, wherein the sulfated polysaccharide agarose conjugate is agarose dextran sulfate.

9. The method as claimed in claim 6, wherein the sulfated polysaccharide agarose conjugate is agarose chondroitin sulfate.

10. The method as claimed in claim 6, wherein the sulfated polysaccharide agarose conjugate is agarose heparin.

* * * * *

UNITED STATES PATENT AND TRADEMARK OFFICE
CERTIFICATE OF CORRECTION

PATENT NO. : 4,138,287
DATED : February 6, 1979
INVENTOR(S) : Lars-Olov Andersson, Gudrun M. Einarsson and Lennart P. Kaplan It is certified that error appears in the above-identified patent and that said Letters Patent are hereby corrected as shown below:

Column 1 line 21, after "Type B" insert -- hepatitis --;

Column 1 line 25, "infention" should read -- infection --; and

Column 1 line 30, "hepititis" should read -- hepatitis --.

Column 2 line 33, "gell" should read -- gel --.

Signed and Sealed this

Tenth Day of July 1979

[SEAL]

Attest:

LUTRELLE F. PARKER
Attesting Officer     Acting Commissioner of Patents and Trademarks